(12) United States Patent
Chen et al.

(10) Patent No.: US 8,329,464 B2
(45) Date of Patent: Dec. 11, 2012

(54) IMPLANT SURFACE TREATMENT METHOD HAVING TISSUES INTEGRATED

(75) Inventors: Wen-Cheng Chen, Tainan County (TW); Chun-Cheng Hung, Kaohsiung (TW); Chia-Ling Ko, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 12/873,536

(22) Filed: Sep. 1, 2010

(65) Prior Publication Data

US 2011/0318835 A1 Dec. 29, 2011

(51) Int. Cl.
| | |
|---|---|
| *C12N 5/00* | (2006.01) |
| *C12N 5/07* | (2010.01) |
| *C12N 5/071* | (2010.01) |
| *C22C 1/00* | (2006.01) |
| *C23C 8/36* | (2006.01) |
| *C21D 1/54* | (2006.01) |
| *C21D 1/70* | (2006.01) |
| *B32B 15/01* | (2006.01) |
| *A61C 8/00* | (2006.01) |

(52) U.S. Cl. ........ 435/325; 435/347; 435/366; 435/371; 435/372; 435/373; 435/377; 435/395; 435/402; 148/95; 148/239; 148/508; 148/516; 148/537; 433/201.1; 623/17.17

(58) Field of Classification Search .................. 435/373; 623/17.17
See application file for complete search history.

(56) References Cited

U.S. PATENT DOCUMENTS

| | | | | |
|---|---|---|---|---|
| 5,934,287 | A * | 8/1999 | Hayashi et al. | 128/898 |
| 5,989,027 | A * | 11/1999 | Wagner et al. | 433/173 |
| 6,069,295 | A * | 5/2000 | Leitao | 623/11.11 |
| 6,095,817 | A * | 8/2000 | Wagner et al. | 433/173 |
| 6,146,686 | A * | 11/2000 | Leitao | 427/2.27 |
| 7,771,774 | B2 * | 8/2010 | Berckmans et al. | 427/2.1 |
| 2002/0143404 | A1 * | 10/2002 | Hayashi et al. | 623/23.57 |
| 2006/0078847 | A1 * | 4/2006 | Kwan | 433/174 |
| 2008/0125868 | A1 * | 5/2008 | Branemark et al. | 623/23.57 |
| 2009/0088858 | A1 * | 4/2009 | Zinger et al. | 623/18.11 |
| 2010/0010632 | A1 * | 1/2010 | Bourges et al. | 623/16.11 |
| 2010/0042223 | A9 * | 2/2010 | Zinger et al. | 623/18.11 |

OTHER PUBLICATIONS

Kubo et al., Cellular behavior on TiO2 nanonodular structures in a micro-to-nanoscale hierarchy model. Biomaterials, vol. 30, pp. 5319-5329, 2009.*
Guehennec et al., Surface treatments of titanium dental implants for rapid osseointegration. Dental Materials, vol. 23, pp. 844-854, 2007.*
Guehennec et al., Osteoblastic cell behaviour on different titanium implant surfaces. Acta Biomaterialia, vol. 4, pp. 535-543, 2008.*
Citeau et al., In vitro biological effects of titanium rough surface obtained by calcium phosphate grid blasting. Biometerials vol. 26, pp. 157-165, 2005.*
Darvell et al., Contamination of titanium castings by aluminium oxide blasting. Journal of Dentistry, vol. 23, No. 5, pp. 319-322, 1995.*
Hewitt et al., Effect of tumour promoters and non-genotoxic carcinogens on terminal differentiation and proliferation in mouse teratoma XB2 cells cultured in low calcium medium. Carcinogenesis, vol. 11 No. 3 pp. 371-375, 1990.*
Klein et al., Improvement of epidermal adhesion by surface modification of craniofacial abutments. Int J Oral and Maxillofacial Implants, vol. 15 No. 2 pp. 247-251, 2000.*
Ronold et al., A study on the effect of dual blasting with TiO2 on titanium implant surfaces on functional attachment in bone. Journal of Biomedical Materials Research. vol. 67A, pp. 524-530, 2003.*
Albrektsson et al., The interface zone of inorganic implants in vivo: titanium implants in bone. Annals of Biomedical Engineering, vol. 11, pp. 1-17, 1983.*
Teng, Fu-Yuan et al., A Comparison of Epithelial Cells, Fibroblasts, and Osteoblasts in Dental Implant Titanium Topographies, Bioinorganic Chemistry and Applications, vol. 2012, Article ID 687291, 2012, pp. 1-9.

* cited by examiner

*Primary Examiner* — Ardin Marschel
*Assistant Examiner* — Addison D Ault
(74) *Attorney, Agent, or Firm* — Jackson IPG PLLC

(57) ABSTRACT

The present disclosure uses different kinds of surface treatment processes on titanium-made dental implants. The growth and attachment conditions of bone cells (MC3T3-E), fibroblasts (NIH 3T3) and epidermal cells (XB-2) on the metal surface of titanium slices with different surface treatments are observed. Tetra-calcium phosphate is used to perform secondary sand-blasting process to clean up the metal surface and provide calcium ions for osteoblastoma physiology. Thus, by adjusting the cells adhesive and proliferative abilities, the success rate of the clinical applications in dental implant is improved.

8 Claims, 11 Drawing Sheets

IMPLANT SURFACE TREATMENT METHOD HAVING TISSUES INTEGRATED

TECHNICAL FIELD OF THE DISCLOSURE

The present disclosure relates to implant surface treatment; more particularly, relates to treating the surface of an implant stem or abutment to be optimal for growth of a bone cell (MC3T3-E1), a fibroblast (NIH 3T3) and an epidermal cell (XB-2) wherein calcium ions are provided for improving implant success.

DESCRIPTION OF THE RELATED ARTS

Titanium (Ti) metal or Ti alloy has good mechanical strength, chemical stability and biological compatibility, and thus is widely used in dental implantation for its good corrosion resistance ability. But, high density of aluminum ions from Ti alloy may relates to Alzheimer's disease; and vanadium from Ti alloy may cause toxicity in cell. Since the biological compatibility of Ti metal is strongly related to oxidized surface structure, surface type and chemical composition, different metal surface treatments are developed for better surface characteristics and stronger binding between implant and bone tissues.

Many methods are used in creating a rough implant surface, like plasma-spraying, grit-blasting, acid etching and anodization. Titanium plasma-spraying (TPS) and grit-blasting create three dimensional roughness implant surface for improving bone anchorage; however, harmful metal ions dissolution or particles, such as aluminum, remains and leads to local or systemic toxic effects. Another widely used method for creating rough implant surface is to use strong acids, like HCl or $H_2SO_4$, which creates a more homogeneous microporous surface than titanium plasma-spraying. Recently, sand-blasting and acid etching (SLA) are used for better early osseointegration and less bone loss than using TPS or acid etching only.

However, because implant surface treatment usually concerns integration for bone tissues only and neglects epidermal cell and fibroblast, the surface for contacting the implant and the whole tissues becomes unlike the original design and makes the implantation fail. Hence, the prior arts do not fulfill all users' requests on actual use.

SUMMARY OF THE DISCLOSURE

The main purpose of the present disclosure is to identify the optimal surface treatments for an implant stem or abutment by treating the implant and then testing it for growth of a bone cell, a fibroblast cells and an epidermal cell using the following tissue culture cells: MC3T3-E1, NIH 3T3 and XB-2. Surface treatments include the use of calcium ions provided for enhancing implant success by enhancing the growth of the bone cells on the part of the implant which would be in contact with bone and inhibiting the growth of the fibroblast in the same area.

The second purpose of the present disclosure is to optimize surface treatment to integrate oral tissues on the treated implant surface where, from top to bottom, the conditions of the surface are smooth; then rough or smooth; and then rough with calcium ions and phosphate ions added.

The third purpose of the present disclosure is to prevent bacterial infection in an oral environment and inhibit growth of the fibroblast for providing a good environment for bone integration and avoiding fibrous encapsulation of the implant.

To achieve the above purposes, the present disclosure is an implant surface treatment method having tissues integrated, comprising steps of: (a) treating a Ti metal surface of an implant through an SLA surface treatment to obtain different roughness; (b) using tetracalcium phosphate (TTCP) to clean and be embedded into the Ti metal through secondary grit-blasting, where TTCP provides calcium ions and phosphate ions; (c) culturing MC3T3-E1, NIH 3T3 and XB-2 to obtain surface conditions suitable for growth and adhesion of the bone cell, the fibroblast and the epidermal cell; and (d) through various surface treatments, adjusting to balance growth velocities of the bone cell, the fibroblast and the epidermal cell between oral tissues and the implant, where growth of the bone cell is impelled and growth of the fibroblast is inhibited. Accordingly, a novel implant surface treatment method having tissues integrated is obtained.

BRIEF DESCRIPTIONS OF THE DRAWINGS

The present disclosure will be better understood from the following detailed description of the preferred embodiment according to the present disclosure, taken in conjunction with the accompanying drawings, in which FIG. 1 is the view showing growth and adhesion of the bone cell, the fibroblast and the epidermal cell;

DESCRIPTION OF THE PREFERRED EMBODIMENT

The following description of the preferred embodiment is provided to understand the features and the structures of the present disclosure.

Figure 1:
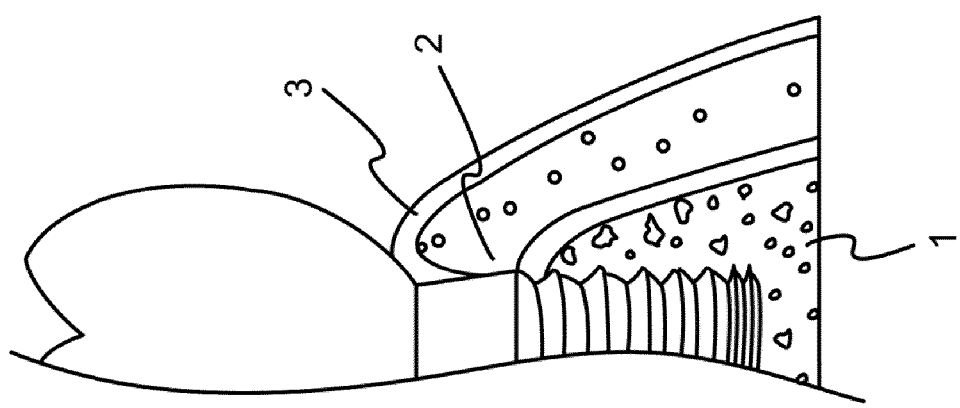

Please refer to FIG. 1, which is a view showing growth and adhesion of a bone cell, a fibroblast and an epidermal cell. As shown in the figure, the present disclosure is an implant surface treatment method having tissues integrated, where different surface treatments are applied to an implant having a titanium (Ti) metal surface, comprising the following steps:

(a) A Ti metal surface of an implant is treated through a sandblasted, large-grit, acid-etched (SLA) surface treatment to obtain different roughness.

(b) Tetracalcium phosphate (TTCP) is used for cleaning and being embedded into the Ti metal through secondary grit-blasting, where TTCP provides calcium ions; and where growth of the bone cell is promoted and growth of the fibroblast is inhibited.

(c) A bone cell (MC3T3-E1), a fibroblast (NIH 3T3) and an epidermal cell (XB-2), which are tissues contacted with the implant, are cultured to find surface conditions suitable for growth and adhesion of the bone cell, the fibroblast and the epidermal cell by observing growth of the tissues.

(d) Through various surface treatments, growth velocities of the bone cell, the fibroblast and the epidermal cell between oral tissues and the implant are adjusted to be balanced for increasing implant success ratio.

If a blasting sand not assimilated to human body is used in grit-blasting, the implant is cleaned by using a material having a smaller particle diameter than that of the blasting sand, where a calcium phosphate salt having a particle diameter of less than micrometers ($\mu m$) is preferred; and where the calcium phosphate salt is $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, $Ca_2H_2P_2O_8$ or their apatite.

On using the present disclosure, a commercial pure Ti is used as a Ti metal sample having a 6 millimeters (mm) length, a 5 mm width and a 1 mm height for an integration test. Some of the samples are buried into epoxy resin to be polished by different sandpapers with ethanol for providing a standard surface roughness by sequentially removing oxidation layer. Then, surface of the samples is washed with acetone and distilled water through ultrasonic oscillation for 5 minutes (min). After being washed, a control group is obtained, where the Ti metal surface is polished to obtain a 0.12 micrometers ($\mu m$) roughness with 5% deviation; and three samples are obtained as a testing group, where surfaces of the samples are mixed with aluminum oxide ($Al_2O_3$) particles to be treated through grit-blasting for 10, 20 and 30 seconds (sec) separately. After grit-blasting, the samples in the testing group are processed through acid etching in solutions for 30 sec. Therein, the grit-blasting process is done by an air compressor with 7 kg/m$^2$ powder blasted at a 0.5 mm distance between the samples and the blasting nozzle; and, the solutions used for acid etching are hydrogen chloride (HCl) and sulfuric acid ($H_2SO_4$).

Figure 2A:
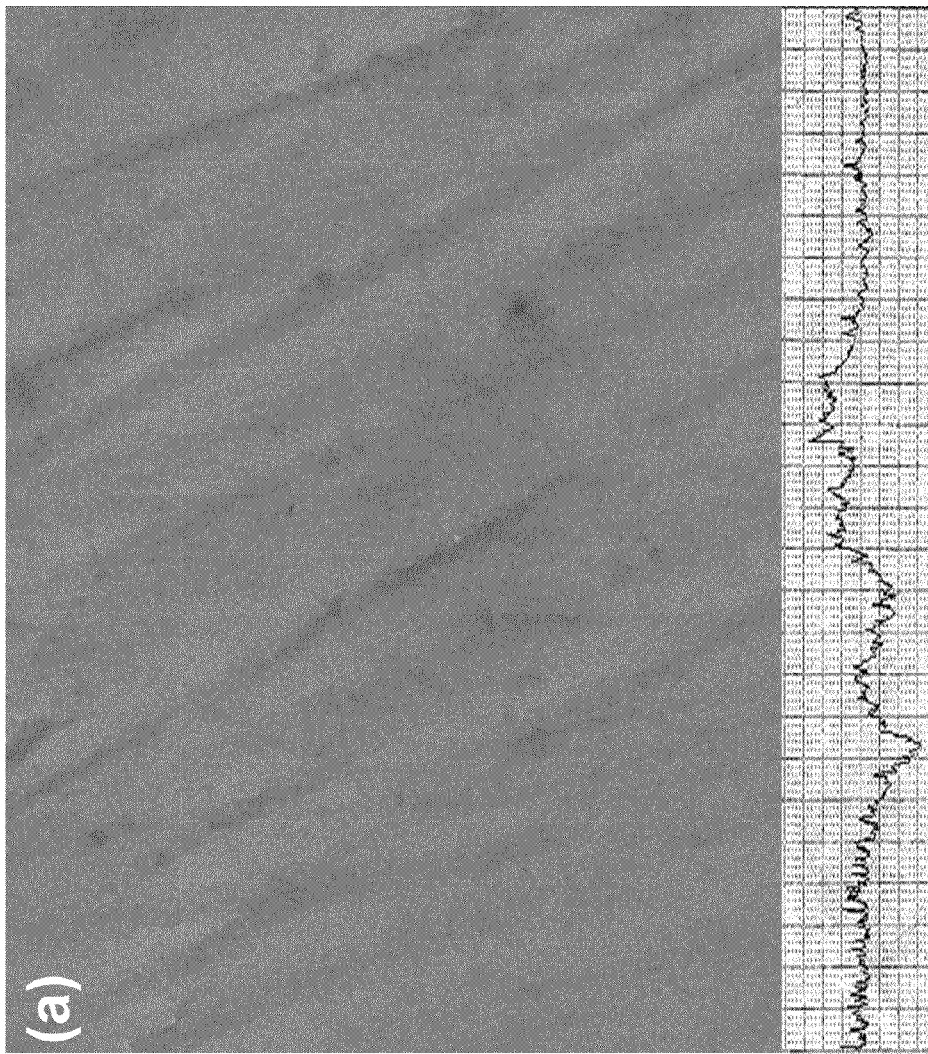
FIG. 2A is the view showing the roughness of the control group.
Figure 2B:
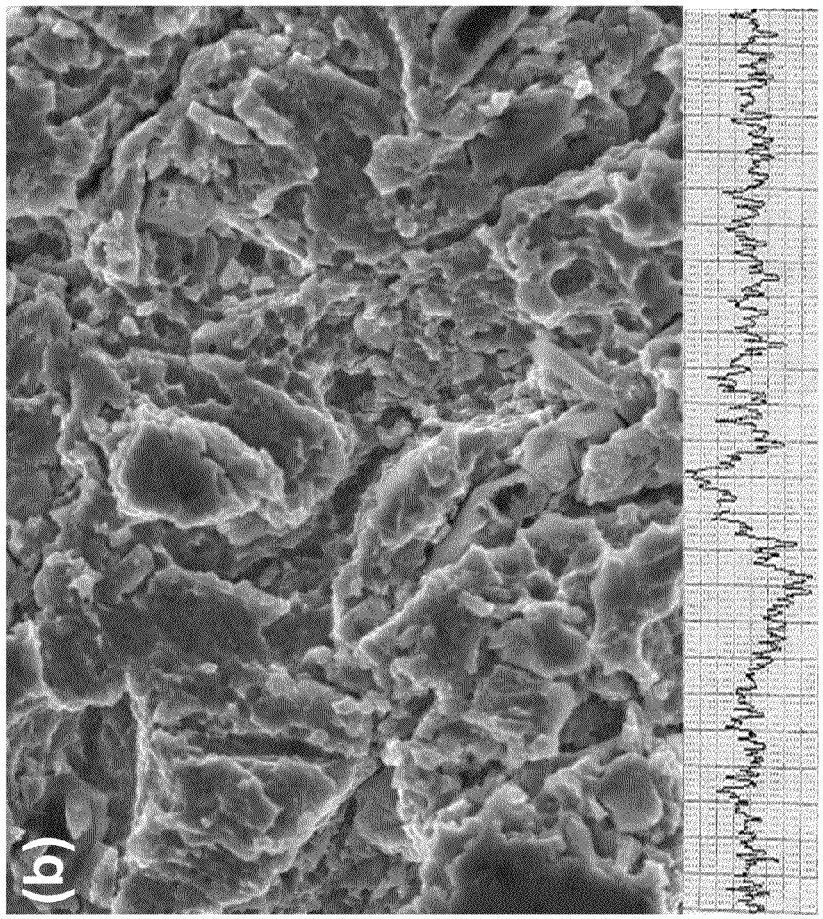
FIG. 2B is the view showing the roughness after 10/30 sec of blasting/etching.
Figure 2C:
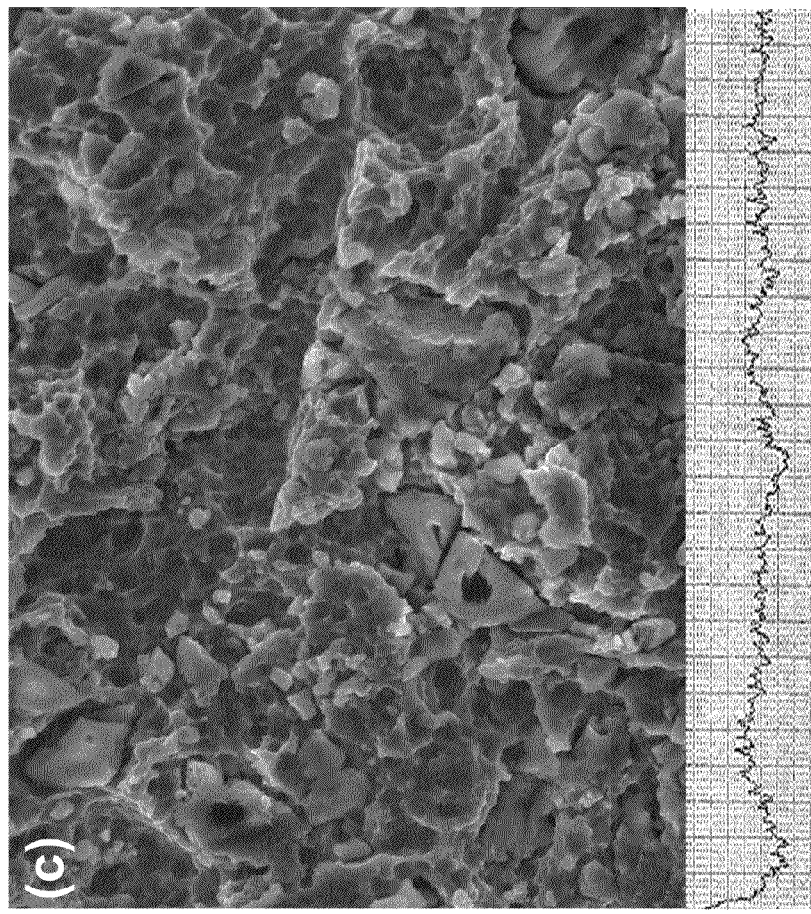
FIG. 2C is the view showing the roughness after 30/30 sec of blasting/etching.
Figure 2D:
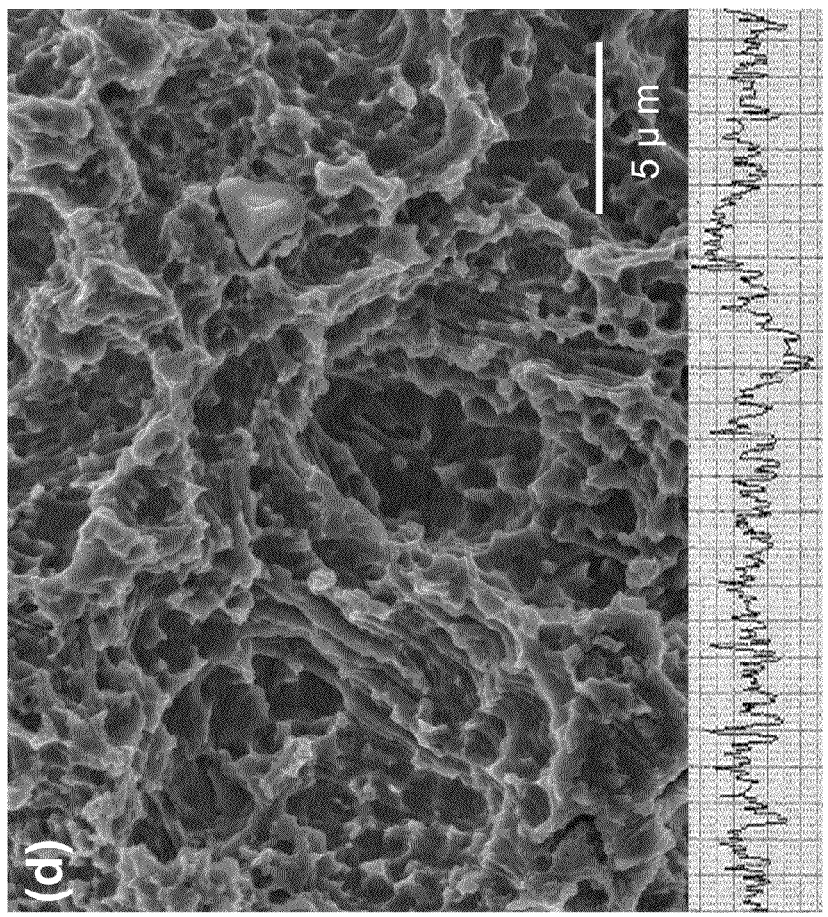
FIG. 2D is the view showing the roughness after 60/30 sec of blasting/etching.

Please further refer to FIG. 2A to FIG. 2D, which are a view showing a roughness of a control group; and views showing roughness after 10/30 sec, 30/30 sec and 60/30 sec of blasting/etching. As shown in the figures, the control group is not processed through grit-blasting and etching and so is very flat with a 0.12 $\mu m$ roughness (Ra) (shown in FIG. 2A). The test group is separately processed through 30 sec of acid etching after 10 sec and 30 sec of grit-blasting to obtain average roughness of 0.67 $\mu m$ and 0.69 $\mu m$, where similar roughness value are observed under gross examination through line scanning (shown in FIG. 2B and FIG. 2C). In FIG. 2D, the test group is processed through 30 sec of acid etching after 60 sec of grit-blasting to obtain an average roughness of 0.93 $\mu m$. In FIG. 2A to FIG. 2D, $Al_2O_3$ particles are still captured or anchored after 30 sec of acid etching, where 60 sec of grit-blasting obviously increases the roughness on comparing to 10 sec and 30 sec of grit-blasting.

Figure 3A:
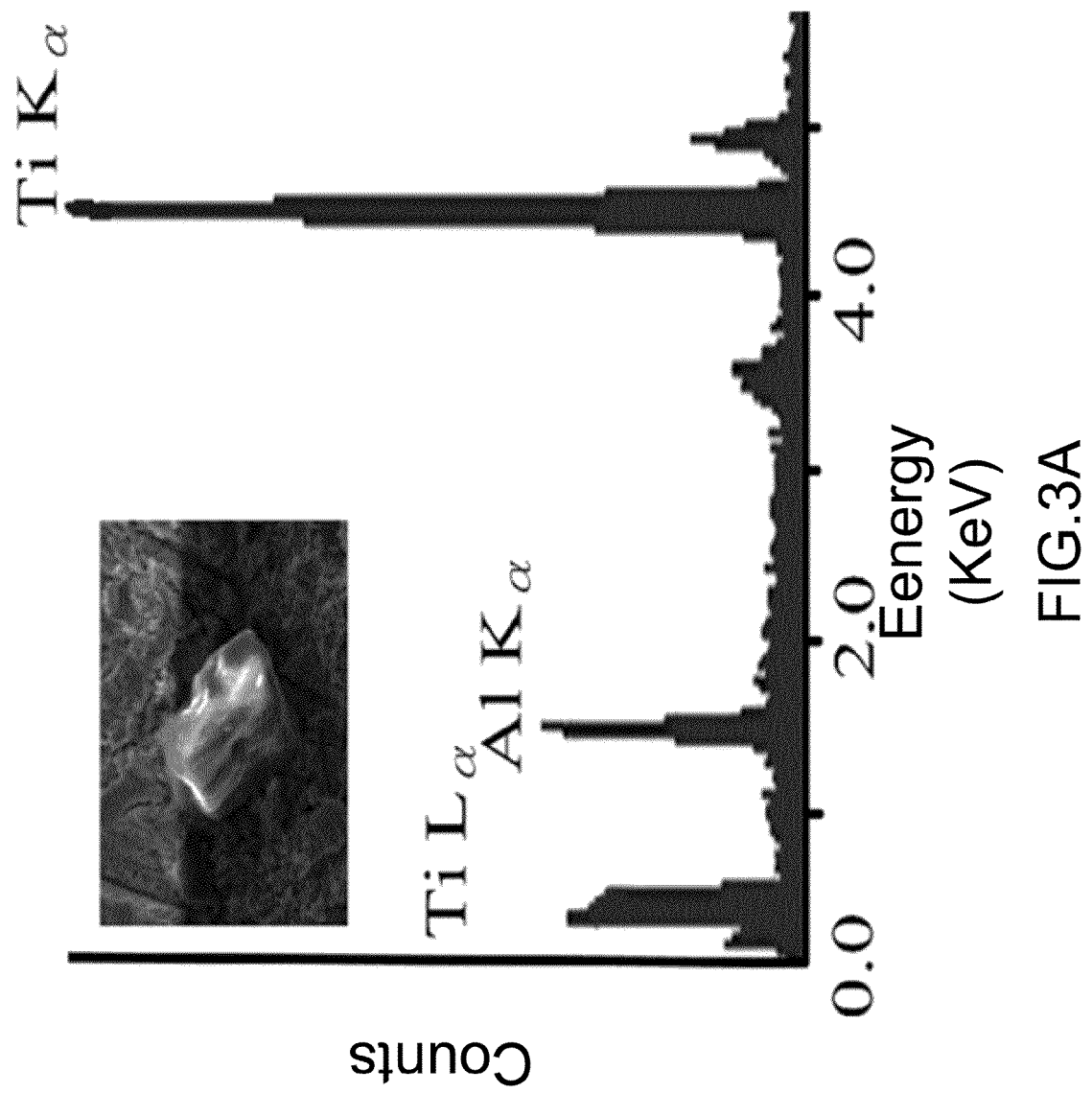
FIG. 3A is the EDS view showing the surface having aluminum oxide ($Al_2O_3$) particles.
Figure 3B:
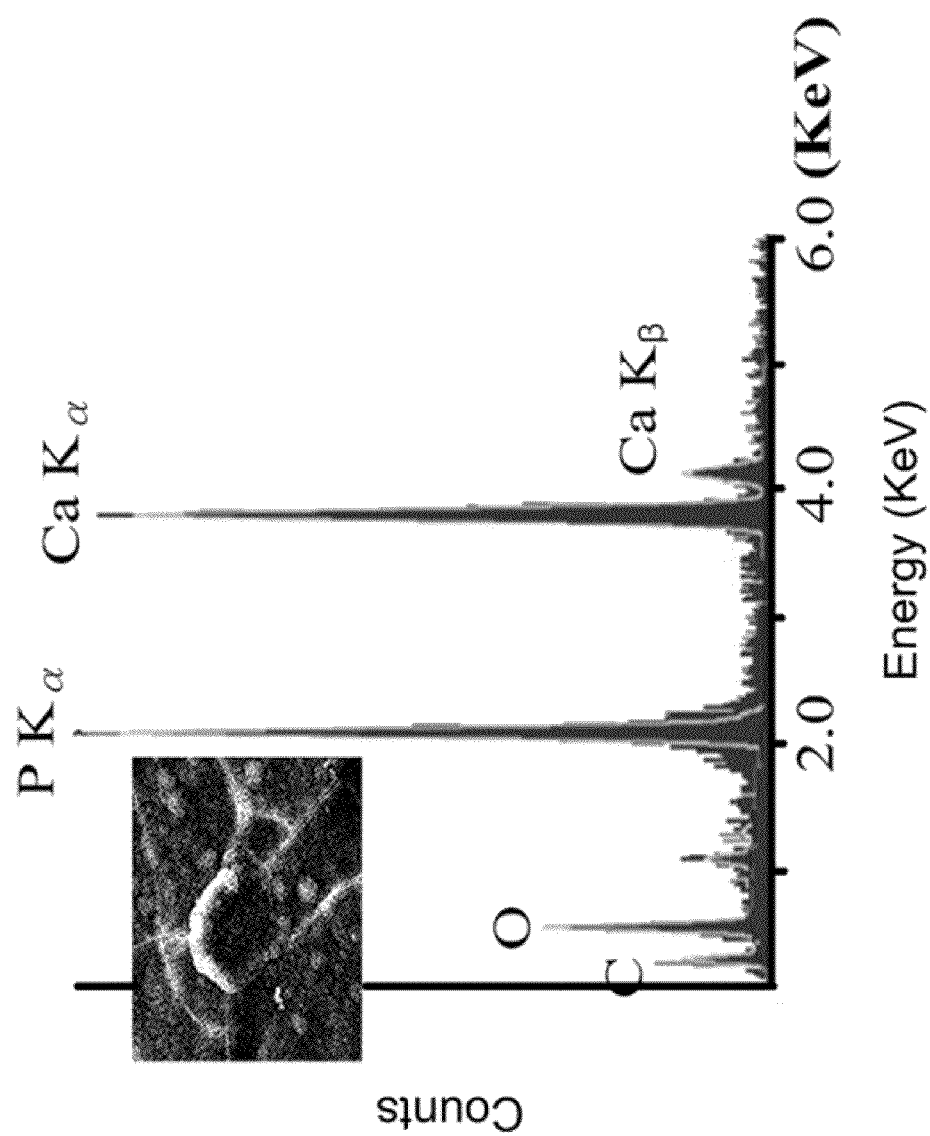
FIG. 3B is the EDS view showing the surface not having $Al_2O_3$ particles.
Figure 4A:
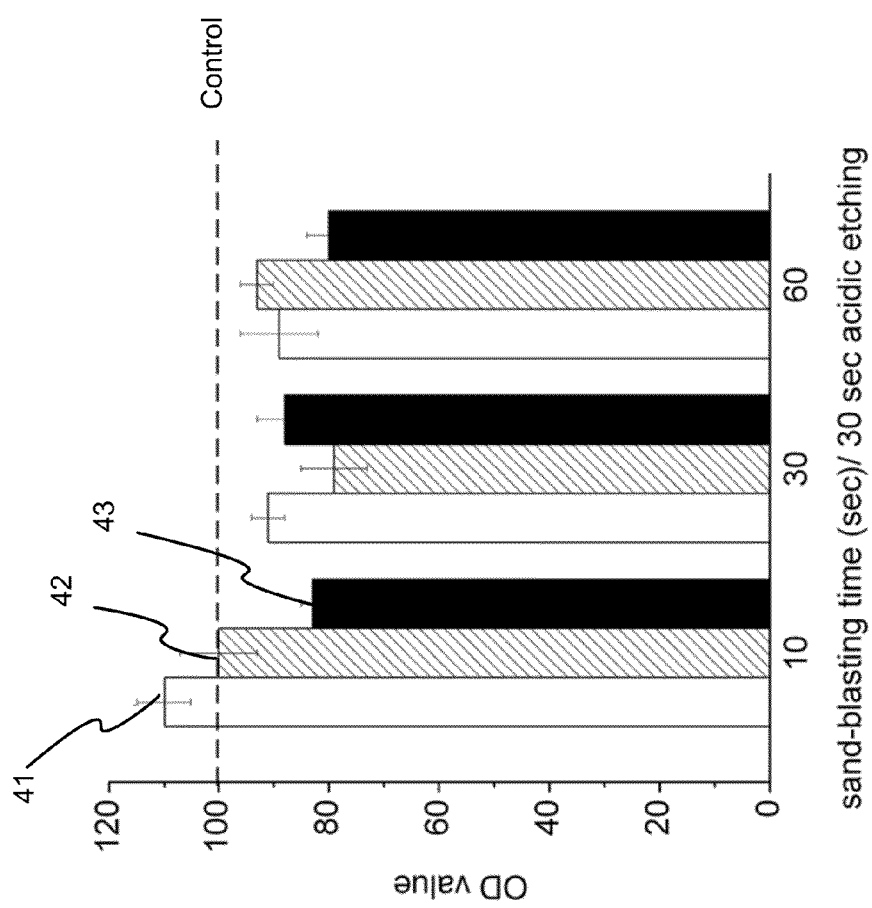
FIG. 4A is the view showing the OD values after 1 hour.
Figure 4B:
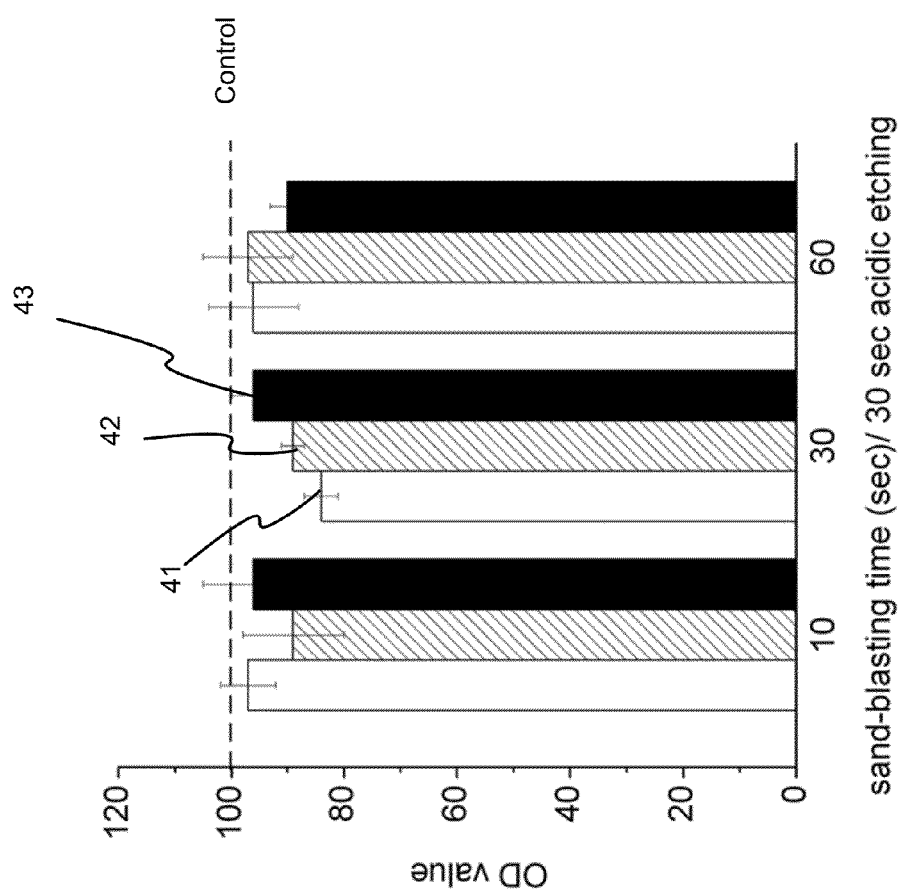
FIG. 4B is the view showing the OD values after 24 hours.
Figure 4C:
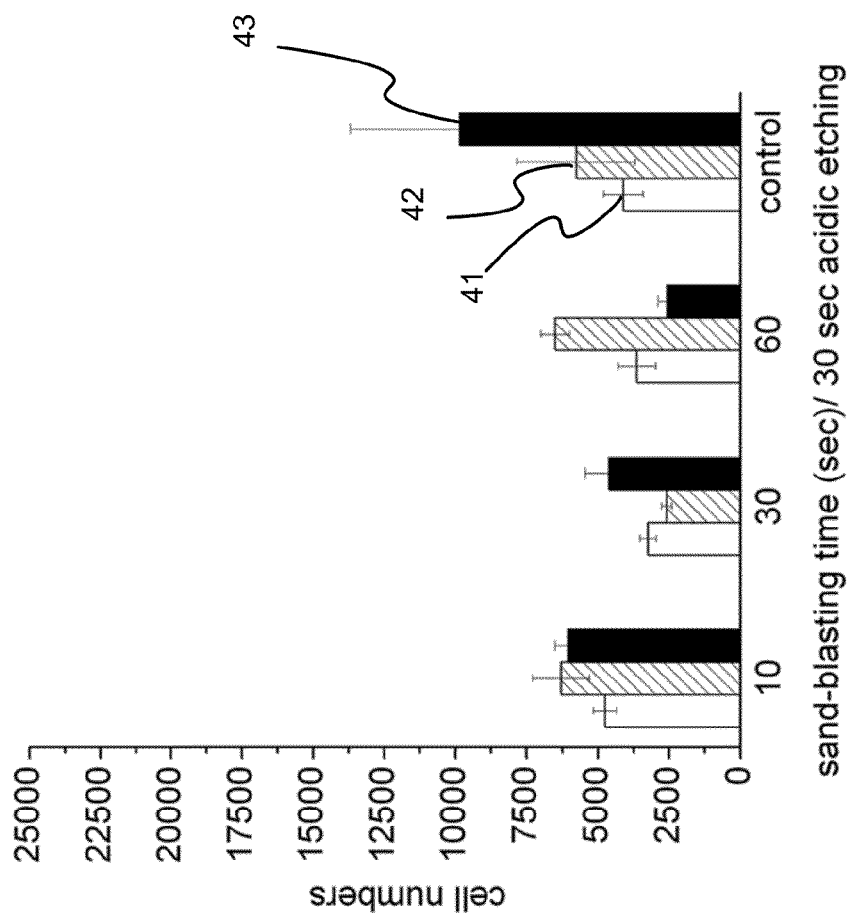
FIG. 4C is the view showing the cell numbers after 1 hour.
Figure 4D:
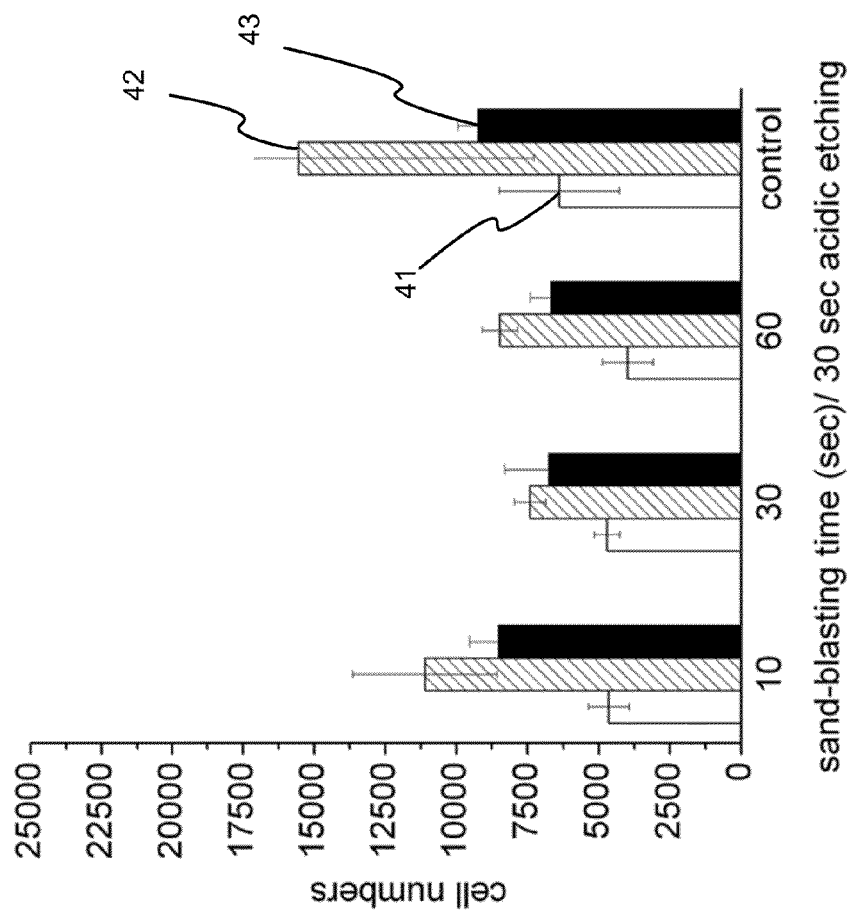
FIG. 4D is the view showing the cell numbers after 24 hours.

Please refer to FIG. 3A and FIG. 3B, which are EDS views showing surfaces having and not having $Al_2O_3$ particles, respectively. As shown in the figures, scanning electron microscopy coupled with energy-dispersive spectroscopy (SEM-EDS) is used for a chemical analysis to obtain composition of residual particles on a sample surface. In FIG. 3A, $Al_2O_3$ particles is remained on the sample surface during 10 sec of grit-blasting and ultrasonic washing accompanied with acid etching does not remove the $Al_2O_3$ particles. However, the $Al_2O_3$ particles are not found on the Ti metal surface in the EDS analysis after the secondary grit-blasting using TTCP particles, where only calcium and phosphorus particles are found. After the TTCP particles having 10 $\mu m$ mean particle diameter are sintered through secondary grit-blasting, the $Al_2O_3$ particles are removed by the TTCP particles while some TTCP particles are left and anchored on the surface to reduce the roughness (mean 0.71, standard deviation 0.16) $\mu m$.

Please refer to FIG. 4A to FIG. 4D, which are views showing OD values after 1 hour and 24 hours; and views showing cell numbers after 1 hour and 24 hours. As shown in the figures, a bone cell, 41, a fibroblast 42 and an epidermal cell 43 are cultured for 1 hour and 24 hours separately to show their growth and adhesion by OD values in FIG. 4A and FIG. 4B. As results show, the situations are similar, which shows the whole environment as under control. Therein, the increase in time for grit-blasting reduces the OD values of the bone cell 41 and the fibroblast 42. On the contrary, the epidermal cell 43 seems not affected. On culturing the epidermal cell 43, adhesion ability on the smooth surface (Ra=0.12) of the control group for the cell after 1 hour is 4 times to adhesion ability on the rough SLA (60/60) surface (Ra=0.93). Yet, by comparing to the cell after 24 hours, the epidermal cell 43 and the fibroblast 42 have different behaviors to surfaces having different roughness. Therein, the fibroblasts 42 (3T3) obtained after 1 and 24 hours in SLA 60/30 do not have obvious change in behavior; but, number of the epidermal cells 43 obtained after 24 hours on a surface with 60/30 SLA treatment greatly grows for 2.6 times to number of the epidermal cells 43 obtained after 1 hour. It shows that the epidermal cell 43 grows faster on a rough surface than on a smooth surface; yet, the fibroblast has a contrary growth tendency to that of the epidermal cell 43.

In another state of use, the epidermal cell 43 is grown on a surface processed through grit-blasting for 60 sec and acid etching for 600 sec to obtain a roughness of Ra=0.74±0.13 $\mu m$ and a good adhesion at an early stage; and, a process of grit-blasting for 30 sec and acid etching for 600 sec obtains a roughness of Ra=0.73±0.12 $\mu m$ and a good growth. The fibroblast 42 is grown on a surface processed through grit-blasting for 30 sec and acid etching for 600 sec to obtain a roughness of Ra=0.73±0.12 $\mu m$ and a good adhesion at an early stage; and, a process of grit-blasting for 30 sec and acid etching for 600 sec also obtains a roughness of Ra=0.73±0.12 $\mu m$ and a good growth. The bone cell 41 is grown on a surface processed through grit-blasting for 10 sec and acid etching for 600 sec to obtain a roughness of Ra=0.64±0.13 $\mu m$ and a good adhesion at an early stage; and, a process of grit-blasting for 60 sec and acid etching for 60 sec obtains a roughness of Ra=1.02±0.08 $\mu m$ and a good growth. Thus, it is found that a process of grit-blasting for 10 sec and acid etching for 30 sec (Ra=0.67±0.07 $\mu m$) is good to the bone cell 41 for adhesion yet is not good to the epidermal cell 43. Adhesion condition of the bone cell becomes bad after grit-blasting with TTCP; but TTCP solution is basically good to the bone cell 41. Hence, it is clear that, on the early stage, surface condition is more important than the effect of ions.

Thus, growth factor of the bone cell 41 and bone matrix are provided in an area for growing the fibroblast, where the area is located within 1~3 mm below a starting place contacted with the skin. Abutment is located within 0.1~1.5 mm in area contacted with the epidermal cell 43 and has a smooth surface for adhering the epidermal cell 43 at the early stage with infection prevented. Following the epidermal cell contact area to 2.9 mm below a starting place contacted with the skin, which is contacted with the fibroblast 42 after contacting with the epidermal cell 43, a 0.2~6 $\mu m$ surface roughness is obtained. Calcium ions and phosphorus ions are provided as growth matrix of the bone cell 41 to inhibit growth of the fibroblast 42 and help growing the bone cell 42. Pores scaled below micrometer are prevented on the contact surface of the bone cell 41 to enhance success ratio of the implant.

The present disclosure considers growth of a bone cell, a fibroblast and an epidermal cell to avoid bacterial infection in an oral environment. In the mean time, calcium ions are provided to inhibit growth of the fibroblast for providing a good bone-integration environment and preventing fibrous encapsulation of the implant. Hence, the present disclosure concerns covering conditions of a bone cell, a fibroblast and an epidermal cell to find a good environment for an implant, where the bone cell is impelled and the fibroblast is inhibited for maintaining a good appearance and preventing implant failure.

To sum up, the present disclosure is an implant surface treatment method having tissues integrated, where a sandblasted, large-grit, acid-etched (SLA) surface treatment is used to form different surface roughness; where a calcium phosphate salt, TTCP, is used for secondarily grit-blasting the Ti metal surface for cleaning and embedding; where a bone cell (MC3T3-E1), a fibroblast (NIH 3T3) and an epidermal cell (XB-2) are cultured to find proper conditions for adhesion and growth of the tissues for improving implant success ratio; and where calcium ions are provided to impel growth of the bone cell and inhibit growth of the fibroblast.

The preferred embodiment herein disclosed is not intended to unnecessarily limit the scope of the disclosure. Therefore, simple modifications or variations belonging to the equivalent of the scope of the claims and the instructions disclosed herein for a patent are all within the scope of the present disclosure.

What is claimed is:

1. An implant surface treatment method to analyze the effects of surface treatment on cell growth, comprising the steps of:
    (a) treating one portion of a surface of a titanium (Ti) metal of an implant through a sandblasted, large-grit, acid-etched (SLA) surface treatment to obtain roughness;
    (b) treating a second portion of a surface of a titanium (Ti) metal of an said implant through a sandblasted, large grit, acid etched (SLA) surface treatment and using a calcium-rich phosphate salt to clean and be embedded into said Ti metal through secondary grit-blasting, wherein the calcium-rich phosphate salt provides calcium ions and phosphate ions;
    (c) leaving a third portion of the surface of a said titanium metal implant untreated;
    (d) culturing a bone cell, a fibroblast and an epidermal cell on the surface of the implant, wherein said bone cell is MC3T3-E1, said fibroblast is NIH 3T3 and said epidermal cell is XB-2, to identify the amount of sandblasting and cleaning to result in activation of growth of said epidermal cell and inhibition of growth of said fibroblast on the third portion of the implant surface, and activation of growth of said bone cell and inhibition of growth of said fibroblast on the second portion of the implant surface; and
    (e) analyzing growth of each of the cell types on the treated implant.

2. The method according to claim 1, wherein said method treats an object selected from a group consisting of an implant stem and an abutment.

3. The method according to claim 1, wherein, on using a blasting sand not assimilated to human body in grit-blasting, said implant is cleaned by using a material having a smaller particle diameter than that of said blasting sand not assimilated to human body; and wherein said material is a calcium-rich phosphate salt having a particle diameter of less than 44 micrometers (μm).

4. The method according to claim 3, wherein said calcium-rich phosphate salt has a calcium-to-phosphate atomic ratio larger than or to equal to the value of 1.5 and is selected from the group consisting of: $Ca_4(PO_4)_2O$, $CaHPO_4 \cdot 2H_2O$, $CaHPO_4$, $Ca_8H_2(PO_4)_6 \cdot 5H_2O$, alpha-$Ca_3(PO_4)_2$, beta-$Ca_3(PO_4)_2$, $Ca_2P_2O_7$, $Ca_2H_2P_2O_8$ and an apatite.

5. The method according to claim 1, wherein, upon implantation into the mouth, the smooth third portion of the implant surface extends 0.1-1.5 mm below the surface of the skin and contacts epidermal cells, and wherein the rough first portion of the implant surface extends below the smooth third portion of the implant surface to a depth of 2.9 mm and contacts fibroblasts, and wherein the rough first portion of the implant surface has a surface roughness of 0.2-6 microns.

6. The method of claim 1, wherein the calcium-rich phosphate salt is tetracalcium phosphate (TTCP).

7. The method of claim 1, wherein from top to bottom, the treatment results in the surface of the implant being smooth, then rough, and then rough with calcium ions and phosphate ions added by the calcium-rich phosphate salt, wherein the calcium-to-phosphate atomic ratio in the calcium-rich phosphate salt is larger than or equal to the value of 1.5.

8. The method of claim 1, wherein the method for analyzing growth is by cell morphology, cell number and/or OD.

* * * * *